US009335167B2

(12) United States Patent
Fukuda et al.

(10) Patent No.: US 9,335,167 B2
(45) Date of Patent: May 10, 2016

(54) APPARATUS FOR MEASURING BODY SIZE AND METHOD OF DOING THE SAME

(75) Inventors: Toshiro Fukuda, Nagasaki (JP); Toshinobu Shigematsu, Nagasaki (JP); Hideki Shimada, Nagasaki (JP); Yoshio Nakamura, Nagasaki (JP)

(73) Assignee: Marinex Corporation, Nagasaki (JP)

( * ) Notice: Subject to any disclaimer, the term of this patent is extended or adjusted under 35 U.S.C. 154(b) by 483 days.

(21) Appl. No.: 13/881,236

(22) PCT Filed: Sep. 21, 2011

(86) PCT No.: PCT/JP2011/071502
§ 371 (c)(1),
(2), (4) Date: Jun. 11, 2013

(87) PCT Pub. No.: WO2012/056831
PCT Pub. Date: May 3, 2012

(65) Prior Publication Data
US 2013/0250082 A1 Sep. 26, 2013

(30) Foreign Application Priority Data
Oct. 26, 2010 (JP) .................................. 2010-239962

(51) Int. Cl.
*H04N 15/00* (2006.01)
*H04N 13/02* (2006.01)
*G06T 17/00* (2006.01)
*G01C 11/10* (2006.01)
(Continued)

(52) U.S. Cl.
CPC .............. *G01C 11/10* (2013.01); *A61B 5/0059* (2013.01); *A61B 5/1072* (2013.01); *A61B 5/1075* (2013.01); *H04N 13/0271* (2013.01); *H04N 13/0275* (2013.01)

(58) Field of Classification Search
None
See application file for complete search history.

(56) References Cited

U.S. PATENT DOCUMENTS

| 5,852,672 | A | * | 12/1998 | Lu | ....................... G01B 11/2441 356/604 |
| 2002/0126295 | A1 | * | 9/2002 | Dudkiewicz | ........... G01B 11/25 356/601 |
| 2004/0017886 | A1 | * | 1/2004 | Kajitani | ............... A61B 5/0064 378/54 |

(Continued)

FOREIGN PATENT DOCUMENTS

| JP | 62-231623 | 10/1987 |
| JP | 7-152984 | 6/1995 |

(Continued)

OTHER PUBLICATIONS

International Search Report (ISR) issued Dec. 20, 2011 in International (PCT) Application No. PCT/JP2011/071502.

Primary Examiner — Christopher S Kelley
Assistant Examiner — Rebecca Volentine
(74) Attorney, Agent, or Firm — Wenderoth, Lind & Ponack, L.L.P.

(57) ABSTRACT

Provided is a body measurement device capable of carrying out a body measurement, such as of abdominal girth or chest girth, with a simple configuration which eliminates moving components. In particular, the body measurement device includes computing device that converts two-dimensional coordinates of images of linear light beams included in images having been captured by a plurality of image capturing devices into two-dimensional coordinates on a certain plane in accordance with a relation stored in a database, and computes a peripheral length of a body of a target person within the certain plane.

12 Claims, 8 Drawing Sheets

(51) Int. Cl.
*A61B 5/00* (2006.01)
*A61B 5/107* (2006.01)

(56) References Cited

U.S. PATENT DOCUMENTS

| | | | |
|---|---|---|---|
| 2004/0083142 A1* | 4/2004 | Kozzinn | A41H 1/00 705/26.5 |
| 2007/0032898 A1* | 2/2007 | Wang | G06Q 30/06 700/132 |
| 2008/0130015 A1* | 6/2008 | Lu | G01B 11/25 356/610 |
| 2009/0310852 A1* | 12/2009 | Cheng | G06T 7/0073 382/154 |
| 2010/0074532 A1* | 3/2010 | Gordon | G01B 11/25 382/203 |
| 2010/0111370 A1* | 5/2010 | Black | G06K 9/00369 382/111 |
| 2010/0157021 A1* | 6/2010 | Abraham | G06Q 30/06 348/47 |
| 2010/0277571 A1* | 11/2010 | Xu | G06T 7/0057 348/47 |
| 2012/0086783 A1* | 4/2012 | Sareen | G06N 3/006 348/47 |

FOREIGN PATENT DOCUMENTS

| | | |
|---|---|---|
| JP | 7-313492 | 12/1995 |
| JP | 2002-222223 | 8/2002 |
| JP | 2009-533 | 1/2009 |
| JP | 4308874 | 5/2009 |
| JP | 4308875 | 5/2009 |

* cited by examiner

APPARATUS FOR MEASURING BODY SIZE AND METHOD OF DOING THE SAME

CROSS-REFERENCE TO RELATED APPLICATION

The present application is based on International Application No. PCT/JP2011/071502 which was filed on Sep. 21, 2011 and claims priority under 35 U.S.C. §119 from Japanese Patent Application No. 2010-239962 which was filed on Oct. 26, 2010.

BACKGROUND OF THE INVENTION

1. Field of the Invention

The invention relates to an apparatus for measuring a body size such as abdominal extension girth or chest girth, and further to a method of doing the same.

2. Description of the Related Art

Recently, there has been developed an apparatus for measuring a body size such as abdominal extension girth or chest girth as a non-contact system, namely, without making contact with a target person. For instance, Japanese Patent Application Publication No. 62 (1987)-231623 suggests an apparatus for automatically measuring a body shape, including a body shape detecting unit including six body shape detectors each of which horizontally detects a distance to a body of a target person from a predetermined location over a certain range, and outputs a signal indicative of the distance, and drivers each of which vertically drives three body shape detectors at a time. The apparatus collects body data output from each of the body shape detectors to thereby have body shape data.

Japanese Patent Application Publication No. 7 (1995)-313492 suggests an apparatus for measuring a body size including light emitting means for emitting laser slit beams, laser beam reflecting means for rotating so as to indirectly irradiate the laser slit beams to a dead angle area of a target person, and image capturing means for capturing images of the emitted laser beams. The apparatus measures a surface and/or a volume of a body on the basis of the obtained data.

The applicant of the present application has suggested the apparatuses for measuring a body size in Japanese Patents Nos. 4308874 and 4308875. The apparatus for measuring a body size, disclosed in Japanese Patent No. 4308874, includes distance measuring means for measuring a distance to a body of a target person, and causes the distance measuring means to run around the target person to thereby measure abdominal extension girth or chest girth. In the apparatus for measuring a body size, disclosed in Japanese Patent No. 4308875, a measurement table on which a target person lies is rotated, and a distance to a body of the target person lying on the measurement table is measured to thereby measure a body size of the target person.

Since the apparatuses disclosed in Japanese Patent Application Publications Nos. 62 (1987)-231623 and 7 (1995)-313492 are large in size and complicated in structure, they cost so much, and hence, it is difficult to introduce them into facilities such as a hospital and a health center, resulting in that they are not spread. Furthermore, since the apparatuses disclosed in Japanese Patents Nos. 4308874 and 4308875 are necessary to include a driver for driving a measurement device and/or a target person, and further, include a movable component, it is not avoidable to carry out complicated maintenance.

SUMMARY OF THE INVENTION

Thus, it is an object of the present invention to provide an apparatus for measuring a body size, and a method of doing the same, both capable of measuring a body size such as abdominal extension girth or chest girth with a simple structure, but without a movable component.

An apparatus for measuring a body size, in accordance with the present invention, includes light emitting devices emitting linear light beams so as to encircle a target person within a certain plane, a plurality of image capturing devices positioned around the target person such that a total circumference of the linear light beams having been emitted to the target person can be captured, and that an optical axis thereof extends obliquely relative to the certain plane, a database storing therein a relation between two-dimensional coordinates on images having been captured by the image capturing devices and two-dimensional coordinates on the certain plane, and a computing device converting two-dimensional coordinates of images of the linear light beams included in images having been captured by the image capturing devices into two-dimensional coordinates on the certain plane in accordance with the relation stored in the database, and computing a peripheral length of a body of the target person within the certain plane.

In the apparatus for measuring a body size, in accordance with the present invention, a plurality of the image capturing devices obliquely captures images of a total circumference of the linear light beams emitted to a target person, an outer shape of a body of the target person within the measurement plane is identified on the basis of the images of the linear light beams captured by the image capturing devices, and a peripheral length of the target person is calculated.

It is preferable that the database divides the certain plane into a plurality of ranges, assigns each of the ranges to each of the image capturing devices, and stores the relation therein for each of the ranges, and the computing device converts two-dimensional coordinates of images of the linear light beams included in images having been captured by the image capturing devices corresponding to the ranges into two-dimensional coordinates on the certain plane in accordance with the relation stored in the database, and computes a peripheral length of a body of the target person in each of the ranges within the certain plane.

It is preferable that the computing device calculates a peripheral length of a body of the target person within the certain plane by totaling the peripheral lengths calculated for each of the ranges.

Thus, the computing device is able to consult the database, and convert, without carrying out complex computation, two-dimensional coordinates of images of the linear light beams included in the captured images into two-dimensional coordinates on the measurement plane to thereby calculate a length of the image of the linear light beams included in images having been captured by the image capturing devices. By summing the calculated lengths, the computing device can readily measure a peripheral length of a body of the target person within the measurement plane.

It is preferable that the database stores therein a second relation between two-dimensional coordinates on images having been captured by the image capturing devices and three-dimensional coordinates including two-dimensional coordinates on the certain plane, in place of or together with the relation.

It is preferable that the computing device forms an image displaying a periphery of the target person within the certain plane.

The present invention further provides an apparatus for measuring a body size, including light emitting devices each emitting linear light beams so as to encircle a target person within a certain plane (hereinafter, called "a measurement plane"), a plurality of image capturing devices positioned around the target person such that a total circumference of the linear light beams having been emitted to the target person can be captured, and that an optical axis of an image capturing optical system of each of the image capturing devices extends obliquely relative to the measurement plane, a database dividing the measurement plane into a plurality of measurement ranges, assigning each of the measurement ranges to each of the image capturing devices, and associating two-dimensional coordinates in each of the measurement ranges on images having been captured by the image capturing devices with two-dimensional coordinates on the measurement plane, two pairs of parallel lines extending perpendicularly to the measurement plane, lines in each of the two pairs being equally spaced away from each other, the database associating first two-dimensional coordinates with second two-dimensional coordinates, the first two-dimensional coordinates being two-dimensional coordinates of an intersection at which the two pairs of parallel lines intersect with each other in each of the measurement ranges on images having been captured by the image capturing devices, the second two-dimensional coordinates being two-dimensional coordinates of an intersection at which the two pairs of parallel lines intersect with each other on the measurement plane in each of the measurement ranges associated with each of the image capturing devices, and a computing device dividing the measurement plane into a plurality of measurement ranges, assigning each of the measurement ranges to each of the image capturing devices, consulting the database to convert two-dimensional coordinates of images of the linear light beams included in images having been captured by the image capturing devices in each of the measurement ranges into two-dimensional coordinates on the measurement plane, respectively, and computing a peripheral length of a body of the target person within the measurement plane.

The present invention further provides a method of measuring a body size, including a first step of emitting linear light beams so as to encircle a target person within a certain plane, a second step of capturing an image of a total circumference of the linear light beams having been emitted to the target person, in a direction oblique to the certain plane, a third step of calculating a relation between two-dimensional coordinates on images having been captured in the second step and two-dimensional coordinates on the certain plane, and a fourth step of converting two-dimensional coordinates of images of the linear light beams included in images having been captured in the second step into two-dimensional coordinates on the certain plane in accordance with the relation, and computing a peripheral length of a body of the target person within the certain plane.

The present invention further provides a computer-readable storage medium containing a set of instructions for causing a computer to carry out a method of measuring a body size, the set of instructions including a first instruction of storing a relation between two-dimensional coordinates on images of a total circumference of linear light beams having been emitted to a target person in a direction oblique to a certain plane such that the target person is encircled by the linear light beams, and two-dimensional coordinates on the certain plane, and a second instruction of converting two-dimensional coordinates of images of the linear light beams included in the captured image into two-dimensional coordinates on the certain plane in accordance with the relation, and computing a peripheral length of a body of the target person within the certain plane.

The advantages obtained by the aforementioned present invention will be described hereinbelow.

In accordance with the present invention, a plurality of the image capturing devices obliquely captures images of a total circumference of the linear light beams emitted to a target person, and a peripheral length of a body of a target person can be calculated, ensuring it possible to measure a body size such as abdominal extension girth or chest girth. It is not necessary to move the image capturing devices and the target person in the apparatus, and furthermore, the apparatus does not include any movable components, ensuring it possible to make measurement at low costs with simple configuration.

The above and other objects and advantageous features of the present invention will be made apparent from the following description made with reference to the accompanying drawings, in which like reference characters designate the same or similar parts throughout the drawings.

DESCRIPTION OF THE PREFERRED EMBODIMENTS

Figure 1:
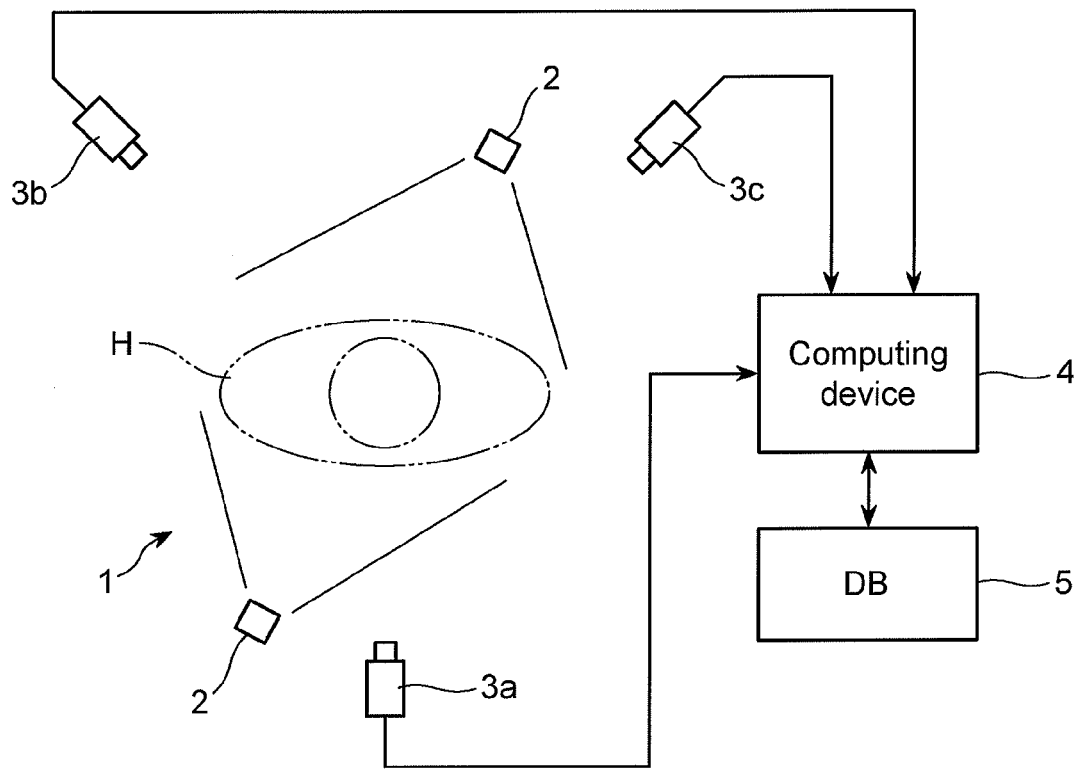
FIG. 1 is a schematic view of the apparatus for measuring a body size, in accordance with the embodiment of the present invention.
Figure 2:
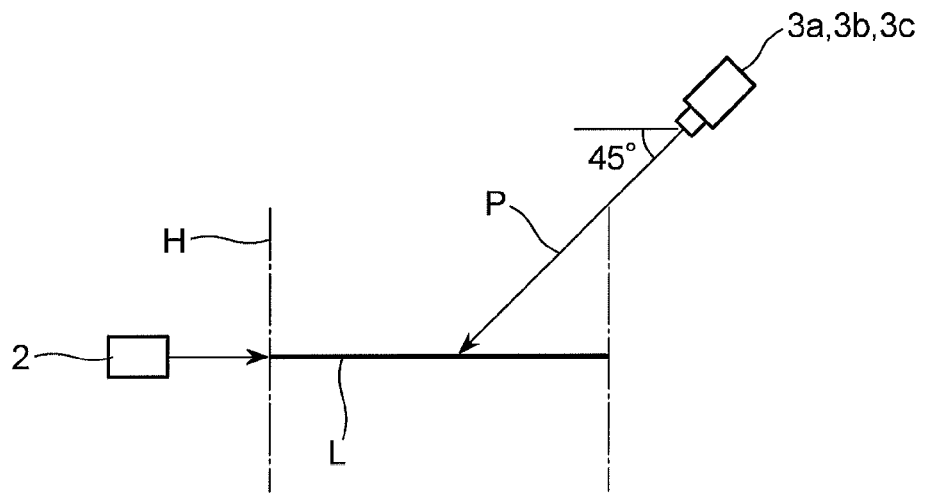
FIG. 2 is a side view showing a position of a camera included in the measurement unit in the apparatus illustrated in FIG. 1.

FIG. 1 is a schematic view of the apparatus for measuring a body size, in accordance with the embodiment of the present invention, and FIG. 2 is a side view showing a position of a camera included in the apparatus illustrated in FIG. 1.

In FIG. 1, the apparatus 1 for measuring a body size, in accordance with the embodiment of the present invention, includes light emitting devices 2 each emitting linear light beam (see FIG. 2) to a target person H, a plurality of image capturing devices 3a, 3b and 3c positioned around the target person H such that images of a total circumference of the linear light beams emitted to the target person H can be captured, a computing device 4 calculating a peripheral length of a body of the target person H on the basis of the images captured by the image capturing devices 3a, 3b and 3c, a database (hereinafter, referred to as "DB") 5 retrieved by the computing device 4.

Each of the light emitting devices 2 is comprised of a laser emitting device which irradiates red laser beams through a horizontally opening slit to thereby emit linear light beams L to the target person H. In FIG. 1, the two light emitting devices 2 are positioned in front of and at rear of the target person H such that they can emit the linear light beams L encircling the target person H within a certain plane. Hereinbelow, a plane defined by the emitted linear light beams L is referred as "a measurement plane". It should be noted that any number of the light emitting devices 2 may be positioned around the target person H, if they can emit the linear light beams L such that the target person H is encircled by the linear light beams L within the certain plane.

The image capturing devices 3a, 3b and 3c are positioned around the target person H such that images of a total circumference of the linear light beams having been emitted to the target person H can be captured. In FIG. 1, the three image capturing devices 3a, 3b and 3c are spaced away from adjacent one by 120 degrees around a vertical axis to encircle the target person H. As illustrated in FIG. 2, an optical axis P of an optical system for capturing images in each of the image capturing devices 3a, 3b and 3c extends obliquely relative to the measurement plane defined by the linear light beams. In the present embodiment, a depression angle of the image capturing devices 3a, 3b and 3c is set to be 45 degrees.

The DB 5 divides the measurement plane into a plurality of measurement ranges, assigns each of the measurement ranges to each of the image capturing devices 3a, 3b and 3c, and associating two-dimensional coordinates on images having been captured by the image capturing devices 3a, 3b and 3c with two-dimensional coordinates on the measurement plane. In the example illustrated in FIG. 3, the measurement plane is divided by 120 degrees into three measurement ranges A, B and C, and the three measurement ranges A, B and C is assigned to the three image capturing devices 3a, 3b and 3c, respectively. FIG. 4 illustrates the image of the measurement plane captured by the image capturing device 3a. The DB 5 records therein the correspondence between two-dimensional coordinates (u, v) for the image illustrated in FIG. 4, and two-dimensional coordinates (X, Z) for the measurement plane illustrated in FIG. 3.

Figure 3:
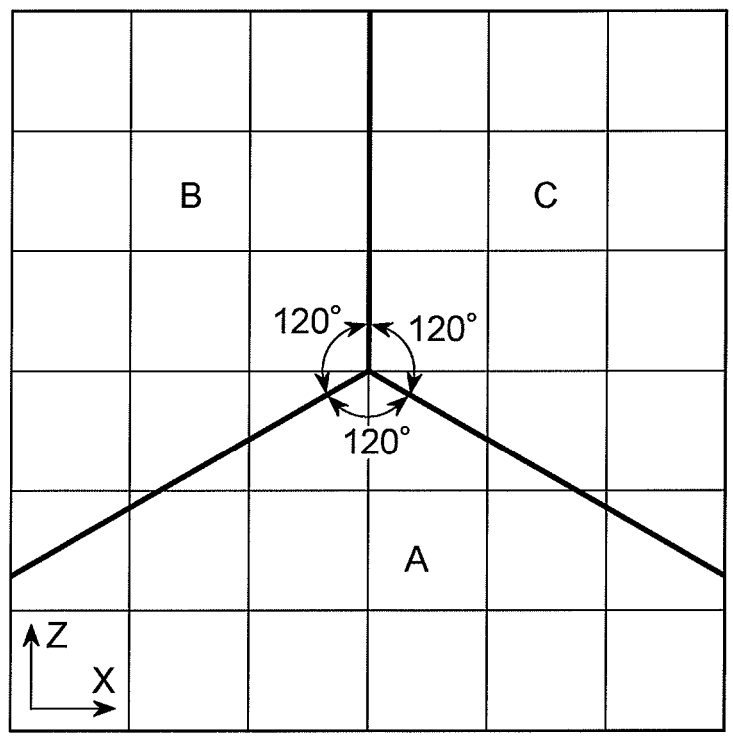
FIG. 3 is a view illustrating an example of division of the measurement plane.
Figure 4:
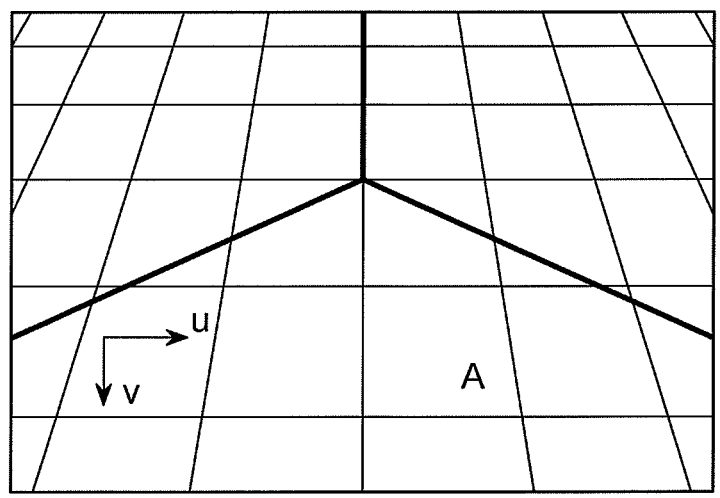
FIG. 4 illustrates an example of an image of the measurement plane illustrated in FIG. 3, captured by the image capturing device.

In designing the DB 5, two sets of parallel lines perpendicular to each other are drawn at an equal pitch on the measurement plane, as illustrated in FIG. 3, and then, the correspondence between two-dimensional coordinates (u, v) of intersections located in the measurement range A of the image having been captured by the image capturing device 3a, illustrated in FIG. 4, and two-dimensional coordinates (X, Z) of intersections located within the measurement range A illustrated in FIG. 3 is recorded into the database. With respect to the measurement ranges B and C, the correspondence is recorded into the database on the basis of the images having been captured by the image capturing devices 3b and 3c, similarly to the measurement range A. The DB 5 may be designed to record therein a correspondence between two-dimensional coordinates (u, v) on the captured image and three-dimensional coordinates (X, Y, Z) including two-dimensional coordinates (X, Z), wherein Y indicates a height of the measurement plane.

The computing device 4 consults the DB 5 to thereby identify the two-dimensional coordinates (X, Z) or the three-dimensional coordinates (X, Y, Z) on the measurement plane on the basis of the two-dimensional coordinates (u, v) of the image of the linear light beams L (the image of the linear light beams L focused on a body of the target person H) included in the captured images within each of the measurement ranges A, B and C corresponding to the image capturing devices 3a, 3b and 3c, respectively, and calculates a peripheral length of a body of the target person H within the measurement plane.

Figure 5:
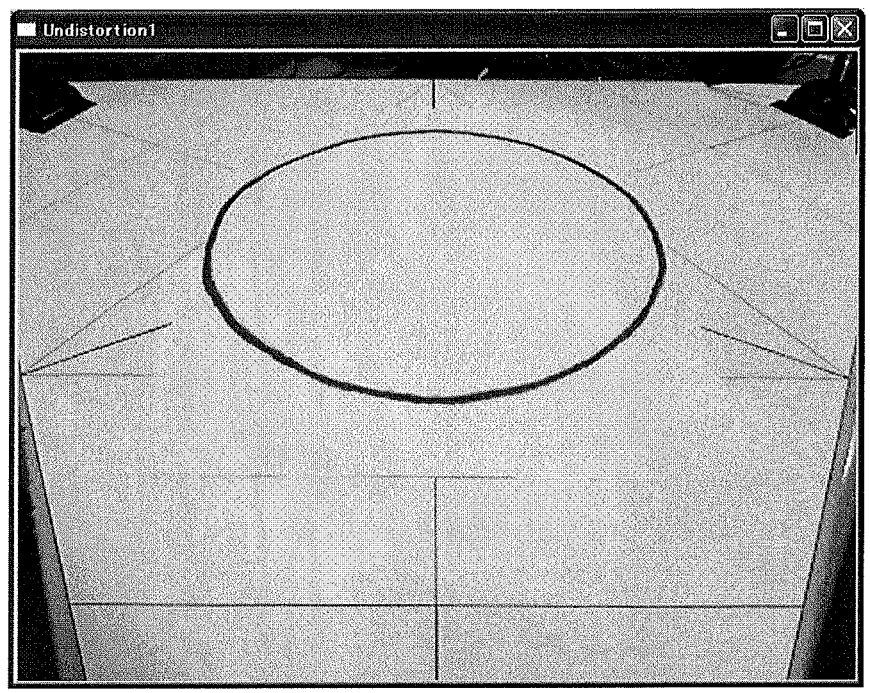
FIG. 5 illustrates an example of an image captured by the image capturing device.
Figure 6:
FIG. 6 illustrates an example in which red is extracted out of the image illustrated in FIG. 5.
Figure 7:
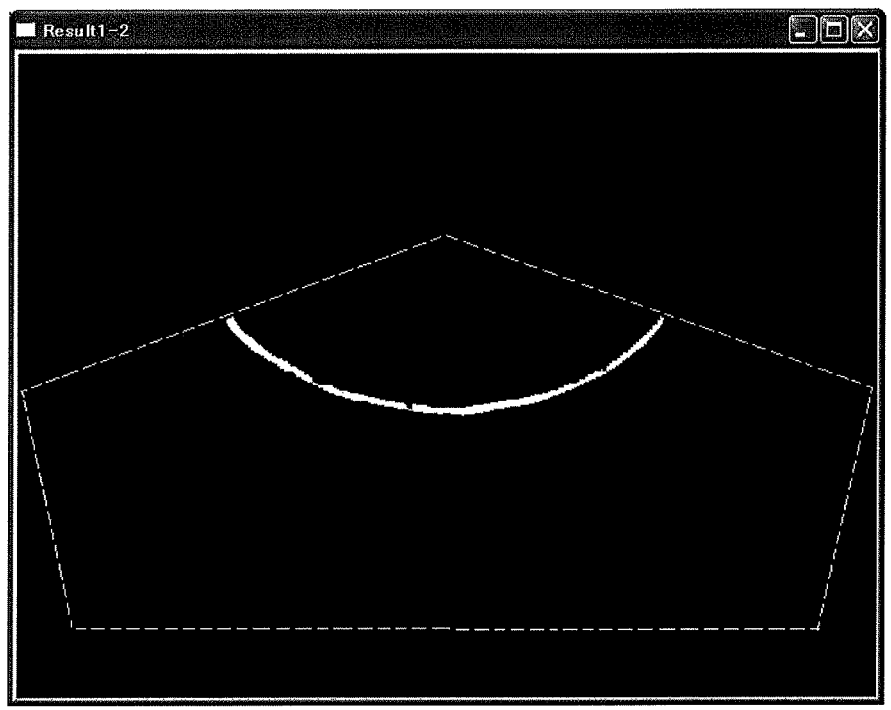
FIG. 7 illustrates an example in which only an image included in a single measurement range is extracted.
Figure 8:
FIG. 8 illustrates an example in which a line defining the captured image illustrated in FIG. 7 is thinned.
Figures 9, 10:
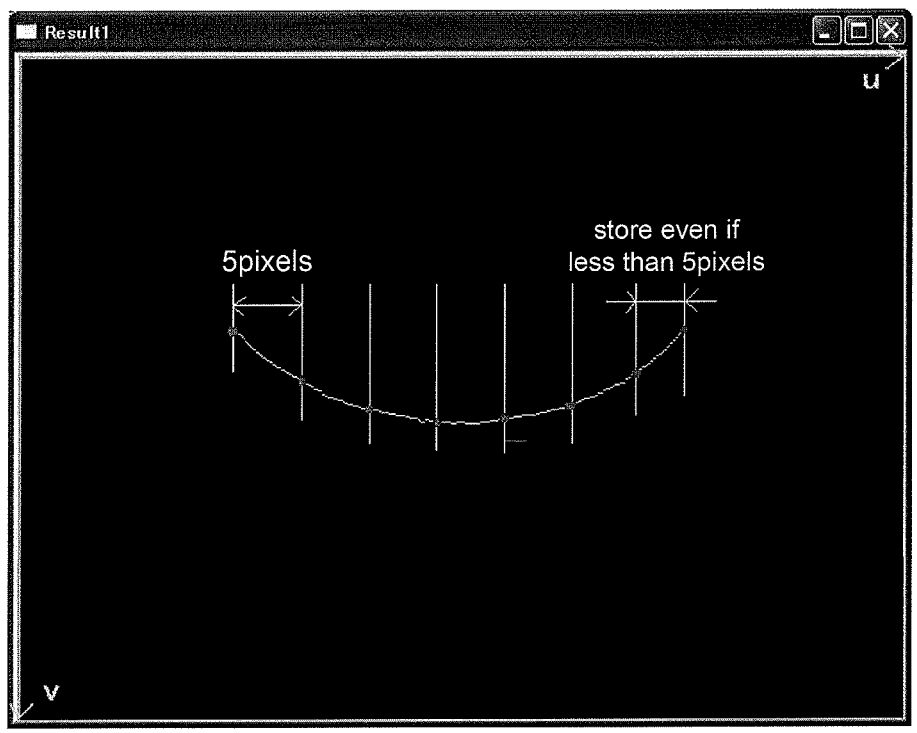
FIG. 9 illustrates an example for obtaining two-dimensional coordinates.
FIG. 10 illustrates extracted two-dimensional coordinates.

FIG. 5 illustrates an example of the image captured by the image capturing device 3a. In the example illustrated in FIG. 5, the image of a red ellipse supposed to be the linear light beams L defined by a periphery of the target person' body is shown. Specifically, the computing device 4 extracts a red line illustrated in FIG. 6 out of the captured image illustrated in FIG. 5, and extracts only the image located within the measurement range A, as illustrated in FIG. 7. Then, as illustrated in FIG. 8, a line of the extracted image is thinned to thereby obtain two-dimensional coordinates (u, v) of the image, as illustrated in FIG. 9. FIG. 10 illustrates an example of the extracted two-dimensional coordinates (u, v).

Figure 11:
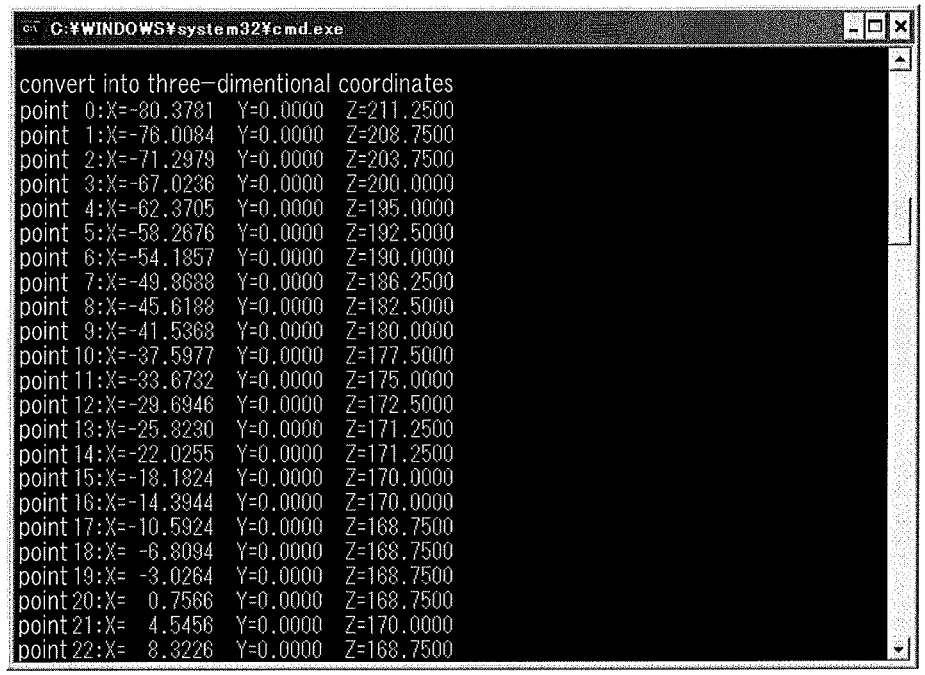
FIG. 11 illustrates an example of conversion to three-dimensional coordinates.
Figure 12:
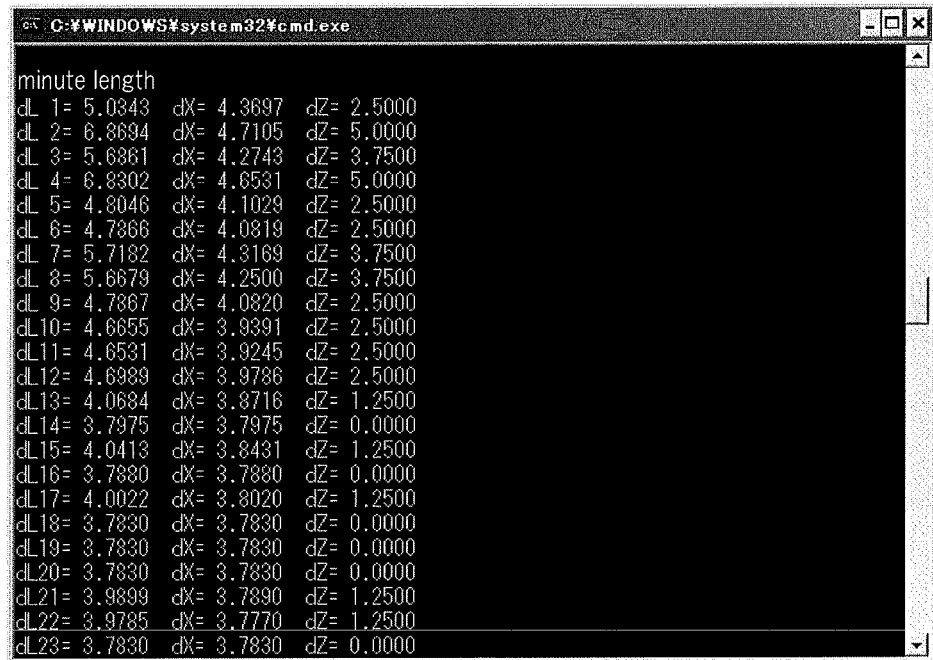
FIG. 12 illustrates an example of calculating a minute length between points.

Then, the computing device 4 consults the DB 5 to thereby convert the thus extracted two-dimensional coordinates (u, v) into three-dimensional coordinates (X, Y=0, Z) (that is, two-dimensional coordinates (X, Z)), as illustrated in FIG. 11. Then, as illustrated in FIG. 12, the computing device 4 calculates a minute length between points identified by the converted coordinates, and further calculates a length of the image of the linear light beams L located within the measurement plane, in accordance with the following equation.

$$L = \sum_{i=1}^{n} dL_i.$$

The computing device 4 carries out computation in the same way with respect to the images having been captured by the image capturing devices 3b and 3c. Then, the computing device 4 sums lengths of the linear light beams L located within the measurement ranges A, B and C to thereby calculate a peripheral length of a body of the target person H within the measurement plane.

Furthermore, the computing device 4 makes an image indicative of a body located within the measurement plane by virtue of the converted coordinates. The computing device 4 makes images of the linear light beams L located within the measurement ranges A, B and C within the measurement plane on the basis of the images having been captured by the image capturing devices 3a, 3b and 3c, and rotates the images to thereby synthesize them.

Figure 13:
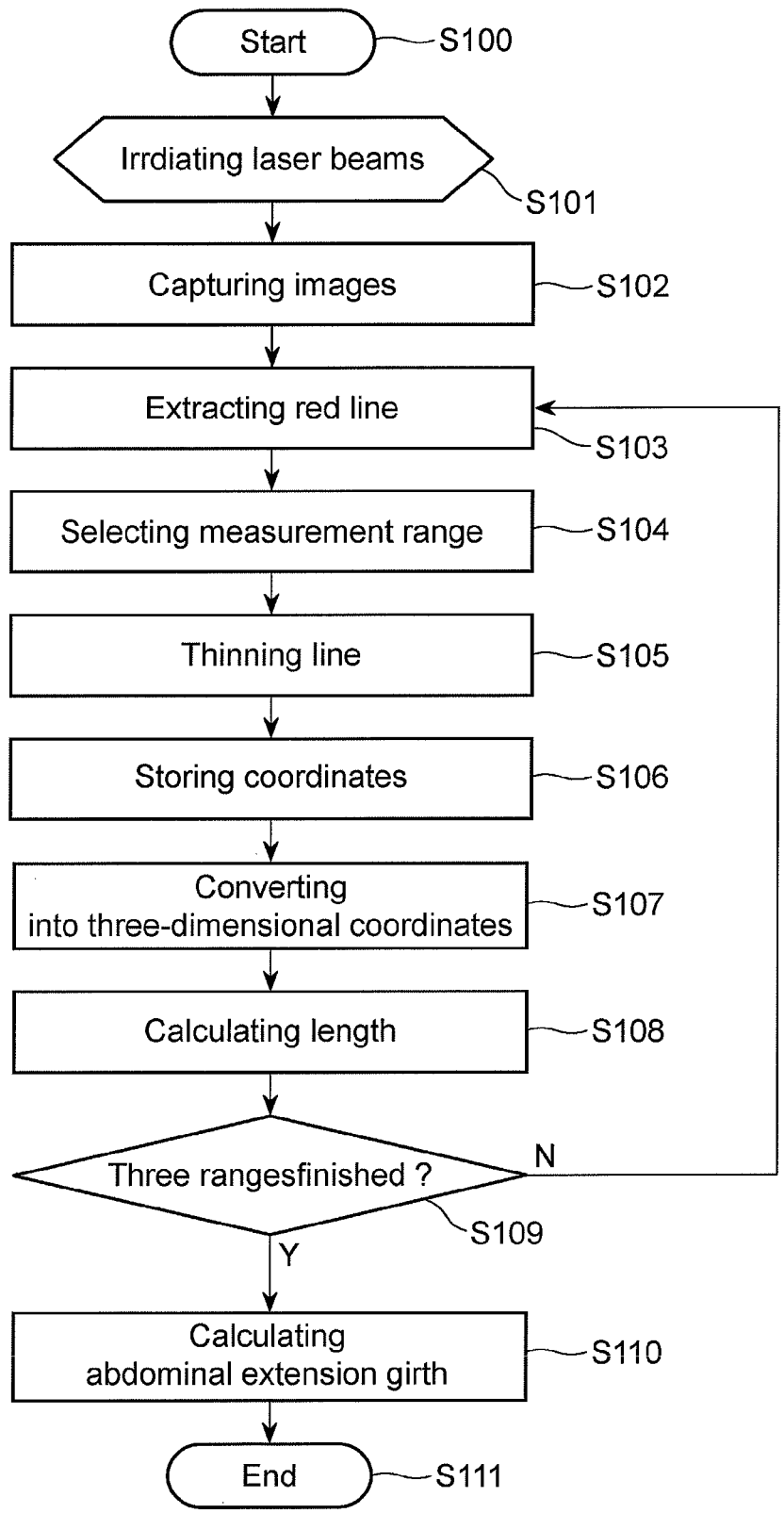
FIG. 13 is a flow-chart showing steps of measuring a body size to be carried out by the apparatus illustrated in FIG. 1.

The steps for measuring a body size, carried out by the apparatus 1 having the above-mentioned structure, are explained hereinbelow. FIG. 13 is a flow-chart showing steps of measuring a body size to be carried out by the apparatus 1. Hereinbelow is explains an example for measuring an abdominal extension girth.

As illustrated in FIG. 13, the apparatus 1 for measuring a body size is caused to start up (S100), and the light emitting devices 2 are caused to irradiate laser beams to an umbilicus of the target person H (S101). Then, the image capturing devices 3a, 3b and 3c capture images (S102) (see FIG. 5). Then, the computing device 4 extracts a red line (S103), as illustrated in FIG. 6, and selects one of the measurement ranges (S104), as illustrated in FIG. 7.

Then, the computing device 4 thins the extracted line (S105), as illustrated in FIG. 8, extracts the coordinates, as illustrated in FIGS. 9 and 10, and stores them in a memory (S106). Then, the computing device 4 converts the extracted coordinates into the three-dimensional coordinates (S107), as illustrated in FIG. 11, and calculates a length of the image of the measurement plane located within the selected measurement range (S108), as illustrated in FIG. 12. The computing device 4 repeatedly carries out the steps S103 to S108 to the three images having been captured by the image capturing devices 3a, 3b and 3c (S109), and finally sums the calculated lengths to thereby calculate an abdominal extension girth of the target person (S110). Thus, the measurement process is finished (S111).

As having been explained so far, in the apparatus 1 for measuring a body size, in accordance with the present embodiment, a plurality of the image capturing devices 3a, 3b and 3c obliquely captures images of a total circumference of the linear light beams L emitted to the target person H, an outer shape of a body of the target person H within the measurement plane is identified on the basis of the images of the linear light beams L included in images captured by the image capturing devices 3a, 3b and 3c, and a peripheral length of the target person H is calculated. It is not necessary in the apparatus 1 to move the image capturing devices 3a, 3b and 3c and the target person H, and furthermore, the apparatus 1 does not include any movable components, ensuring it possible to make measurement at low costs with simple configuration.

Figure 14:
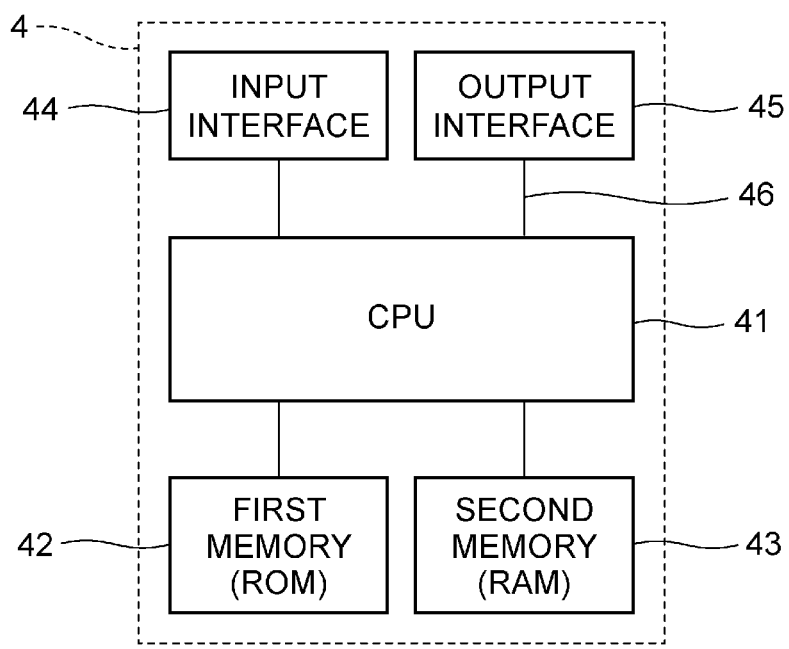
FIG. 14 is a block diagram illustrating an example of the structure of the computing device.

FIG. 14 is a block diagram illustrating an example of the structure of the computing device 4.

As illustrated in FIG. 14, the computing device 4 is comprised of a central processing unit (CPU) 41, a first memory 42, a second memory 43, an input interface 44 through which a command and/or data is input into the central processing unit 41, an output interface 45 through which results of analysis having been executed by the central processing 41 unit is output, and buses 46 through which the central processing unit 41 are electrically connected to other parts.

Each of the first and second memories 42 and 43 is comprised of a semiconductor memory such as a read only memory (ROM), a random access memory (RAM) or an IC memory card, or a storage device such as a flexible disc, a hard disc or an optic magnetic disc. In the present embodiment, the first memory 42 is comprised of ROM, and the second memory 43 is comprised of RAM.

The first memory 42 stores therein both various control programs to be executed by the central processing unit 41 and fixed data. The second memory 43 stores therein various data and parameters, and presents a working area to the central processing unit 41. That is, the second memory 43 stores data which is temporarily necessary for the central processing unit 41 to execute programs.

The central processing unit 41 reads the program out of the first memory 42, and executes the program. Thus, the central processing unit 41 operates in accordance with the program stored in the first memory 42.

INDUSTRIAL APPLICABILITY

The apparatus for measuring a body size, in accordance with the present invention, is useful as an apparatus for measuring various sizes such as abdominal extension girth or chest girth, and suitable as an apparatus for measuring a body size of a target person in non-contact, namely, without making contact with a target person.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

The entire disclosure of Japanese Patent Application No. 2010-239962 filed on Oct. 26, 2010 including specification, claims, drawings and summary is incorporated herein by reference in its entirety.

The invention claimed is:

1. An apparatus for measuring a body size, comprising:
light emitting devices emitting linear light beams so as to encircle a target person within a certain plane;
a plurality of image capturing devices positioned around said target person such that a total circumference of said linear light beams having been emitted to said target person can be captured, and that an optical axis thereof extends obliquely relative to said certain plane;
a database storing therein a relation between two-dimensional coordinates on images having been captured by said image capturing devices and two-dimensional coordinates on said certain plane; and
a computing device converting two-dimensional coordinates of images of said linear light beams included in images having been captured by said image capturing devices into two-dimensional coordinates on said certain plane in accordance with said relation stored in said database, and computing a peripheral length of a body of said target person within said certain plane,
wherein said database divides said certain plane into a plurality of ranges, assigns each of said ranges to each of said image capturing devices, and stores said relation therein for each of said ranges, and
said computing device converts two-dimensional coordinates of images of said linear light beams included in images having been captured by said image capturing devices corresponding to said ranges into two-dimensional coordinates on said certain plane in accordance with said relation stored in said database, and computes a peripheral length of a body of said target person in each of said ranges within said certain plane.

2. The apparatus as set forth in claim 1, wherein said computing device a peripheral length of a body of said target person within said certain plane by totaling the peripheral lengths calculated for each of said ranges.

3. The apparatus as set forth in claim 1, wherein said database stores therein a second relation between two-dimensional coordinates on images having been captured by said image capturing devices and three-dimensional coordinates including two-dimensional coordinates on said certain plane, in place of or together with said relation.

4. The apparatus as set forth in claim 1, wherein said computing device forms an image displaying a periphery of said target person within said certain plane.

5. A method of measuring a body size, comprising:
a first step of emitting linear light beams so as to encircle a target person within a certain plane;
a second step of capturing an image of a total circumference of said linear light beams having been emitted to said target person, in a direction oblique to said certain plane;
a third step of calculating a relation between two-dimensional coordinates on images having been captured in said second step and two-dimensional coordinates on said certain plane; and
a fourth step of converting two-dimensional coordinates of images of said linear light beams included in images having been captured in said second step into two-dimensional coordinates on said certain plane in accordance with said relation, and computing a peripheral length of a body of said target person within said certain plane, wherein said certain plane is divided into a plurality of ranges, and said relation is calculated for each of said ranges in said third step, and two-dimensional coordinates of images of said linear light beams included in images having been captured in correspondence to each of said ranges are converted into two-dimensional coordinates on said certain plane in accordance with said relation, and a peripheral length of a body of said target person is calculated in each of said ranges within said certain plane.

6. The method as set forth in claim 5, wherein a peripheral length of a body of said target person within said certain plane is calculated by totaling the peripheral lengths calculated for each of said ranges in said fourth step.

7. The method as set forth in claim 5, wherein a second relation between two-dimensional coordinates on images having been captured in said second step and three-dimensional coordinates including two-dimensional coordinates on said certain plane is calculated in said third step in place of or together with said relation.

8. The method as set forth in claim 5, further comprising forming an image displaying a periphery of said target person within said certain plane.

9. A non-transitory computer-readable storage medium containing a set of instructions for causing a computer to carry out a method of measuring a body size, the set of instructions comprising:

a first instruction of storing a relation between two-dimensional coordinates on images of a total circumference of linear light beams having been emitted to a target person in a direction oblique to a certain plane such that said target person is encircled by said linear light beams, and two-dimensional coordinates on said certain plane; and a second instruction of converting two-dimensional coordinates of images of said linear light beams included in the captured image into two-dimensional coordinates on said certain plane in accordance with said relation, and computing a peripheral length of a body of said target person within said certain plane, wherein said certain plane is divided into a plurality of ranges, and said relation is calculated for each of said ranges in said first instruction, and two-dimensional coordinates of images of said linear light beams included in images having been captured in correspondence to each of said ranges are converted into two-dimensional coordinates on said certain plane in accordance with said relation, and a peripheral length of a body of said target person is calculated in each of said ranges within said certain plane in said second instruction.

10. The non-transitory computer-readable storage medium as set forth in claim 9, wherein a peripheral length of a body of said target person within said certain plane is calculated by totaling the peripheral lengths calculated for each of said ranges in said second instruction.

11. The non-transitory computer-readable storage medium as set forth in claim 9, wherein a second relation between two-dimensional coordinates on the captured images and three-dimensional coordinates including two-dimensional coordinates on said certain plane is calculated in said first instruction in place of or together with said relation.

12. The non-transitory computer-readable storage medium as set forth in claim 9, wherein said set of instructions further includes forming an image displaying a periphery of said target person within said certain plane.

* * * * *